United States Patent
Chen et al.

(10) Patent No.: US 6,719,703 B2
(45) Date of Patent: Apr. 13, 2004

(54) METHOD AND APPARATUS FOR MEASURING BLOOD PRESSURE BY THE OSCILLOMETRIC TECHNIQUE

(75) Inventors: Yunquan Chen, Delta (CA); Anton Bogdan Zorn, Vancouver (CA); Kevin Daryl Strange, Port Moody (CA)

(73) Assignee: VSM Medtech Ltd., British Columbia (CA)

( * ) Notice: Subject to any disclaimer, the term of this patent is extended or adjusted under 35 U.S.C. 154(b) by 247 days.

(21) Appl. No.: 09/882,908

(22) Filed: Jun. 15, 2001

(65) Prior Publication Data

US 2003/0045801 A1 Mar. 6, 2003

(51) Int. Cl.$^7$ ................................. A61B 5/02
(52) U.S. Cl. ................. 600/494; 600/495; 600/496
(58) Field of Search ................ 600/490–496, 600/500–503

(56) References Cited

U.S. PATENT DOCUMENTS

| | | | |
|---|---|---|---|
| 4,154,238 A | | 5/1979 | Link |
| 4,349,034 A | * | 9/1982 | Ramsey, III ............. 600/494 |
| 4,718,427 A | * | 1/1988 | Russell .................. 600/492 |
| 4,860,760 A | * | 8/1989 | Miyawaki et al. ......... 600/493 |
| 4,984,577 A | * | 1/1991 | Frankenreiter ........... 600/494 |
| 5,054,494 A | * | 10/1991 | Lazzaro et al. ........... 600/490 |
| 5,339,818 A | | 8/1994 | Baker et al. |
| 5,355,890 A | | 10/1994 | Aguirre et al. |
| 5,423,322 A | | 6/1995 | Clark et al. |
| 5,505,206 A | | 4/1996 | Walloch |
| 5,564,426 A | * | 10/1996 | Iwai ..................... 600/493 |
| 5,577,508 A | | 11/1996 | Medero |
| 5,797,850 A | * | 8/1998 | Archibald et al. ........ 600/494 |
| 5,961,467 A | * | 10/1999 | Shimazu et al. ......... 600/494 |
| 5,971,932 A | | 10/1999 | Okamoto |
| 5,993,394 A | | 11/1999 | Poliac |
| 6,099,477 A | | 8/2000 | Archibald et al. |

OTHER PUBLICATIONS

Moraes, JCTB et al., Development of a New Oscillometric Blood Pressure Measurement System, *Computers in Cardiology*, 1999, pp. 467–470.

Moraes, JCTB et al., A Strategy for Determination of Systolic, Mean and Diastolic Blood Pressures for Oscillometric Pulse Profiles, *Computers in Cardiology*, 2000, pp. 211–214.

"Handbook of Blood Pressure Measurement", L.A. Geddes, Mar. 1991, Humana Press, Publisher, ISBN: 0–89603–194–2 (Geddes 91).

"Characterization of the Oscillometric Method for Measuring Indirect Blood Pressure", L.A. Geddes et al. Annals of Biomedical Engineering, vol. 10, pp. 271–280, 1982 (Geddes 82).

\* cited by examiner

*Primary Examiner*—Joseph Pelham
(74) *Attorney, Agent, or Firm*—Oyen Wiggs Green & Mutala

(57) ABSTRACT

A method and apparatus for measuring blood pressure by the oscillometric technique. The method incorporates variable PIP's. The method comprises the steps of obtaining a value for the peak amplitude $A_{max}$ of an oscillometric envelope; determining a cuff pressure, CP, which corresponds in time with $A_{max}$, this pressure representing the MAP of the subject; computing a variable value $PIP_{SBP}$ as a function of MAP; performing the calculation $A_{sbp}=A_{max}*PIP_{SBP}$ to determine a systolic amplitude value $A_{sbp}$ along the oscillometric envelope; and determining the cuff pressure C which corresponds in time to $A_{sbp}$, this value representing the systolic blood pressure (SBP) of the subject. PIP can be calculated using a piece-wise linear, polynomial, exponential or other function.

22 Claims, 7 Drawing Sheets

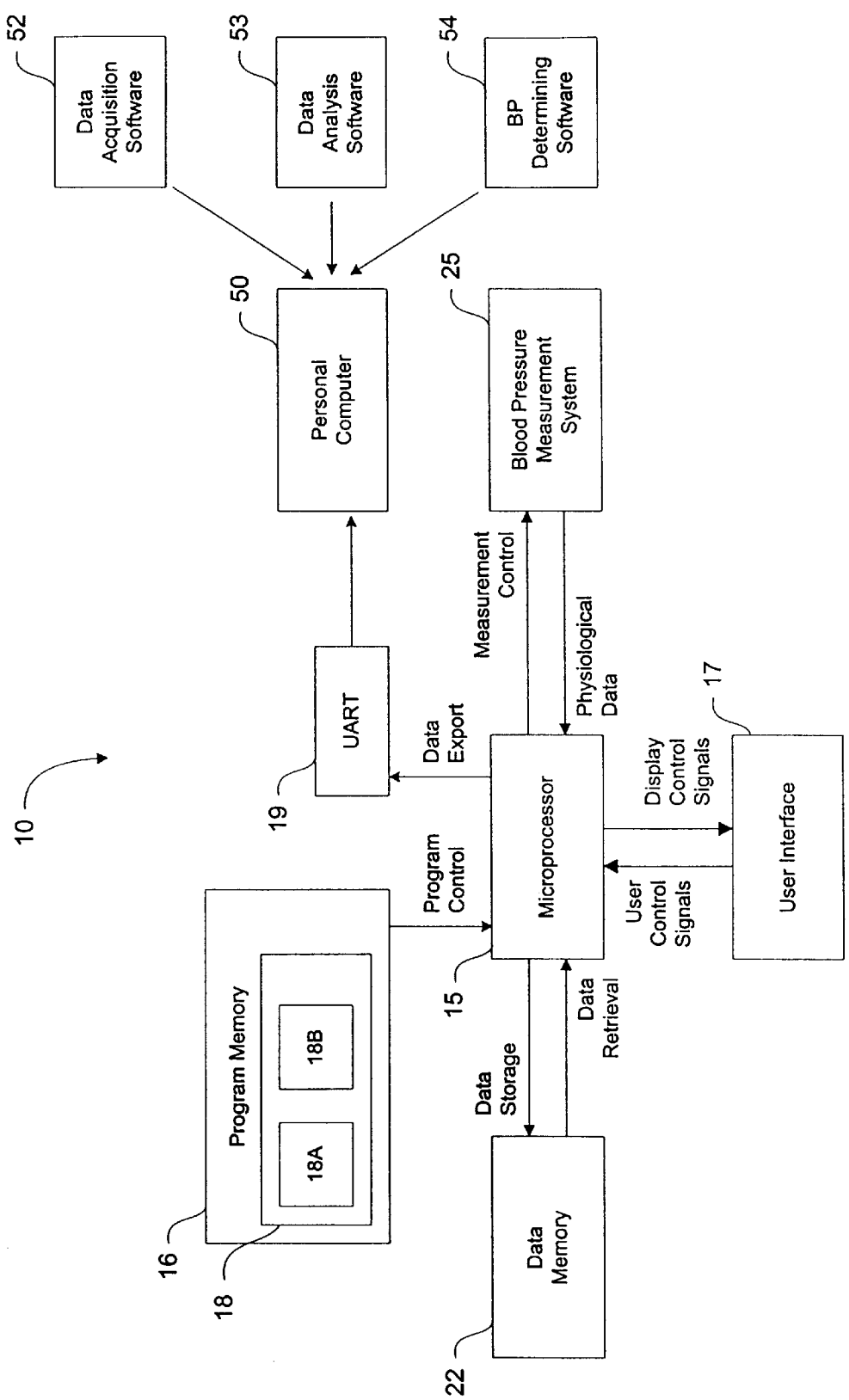
Figure 2. A Block Diagram of the Apparatus

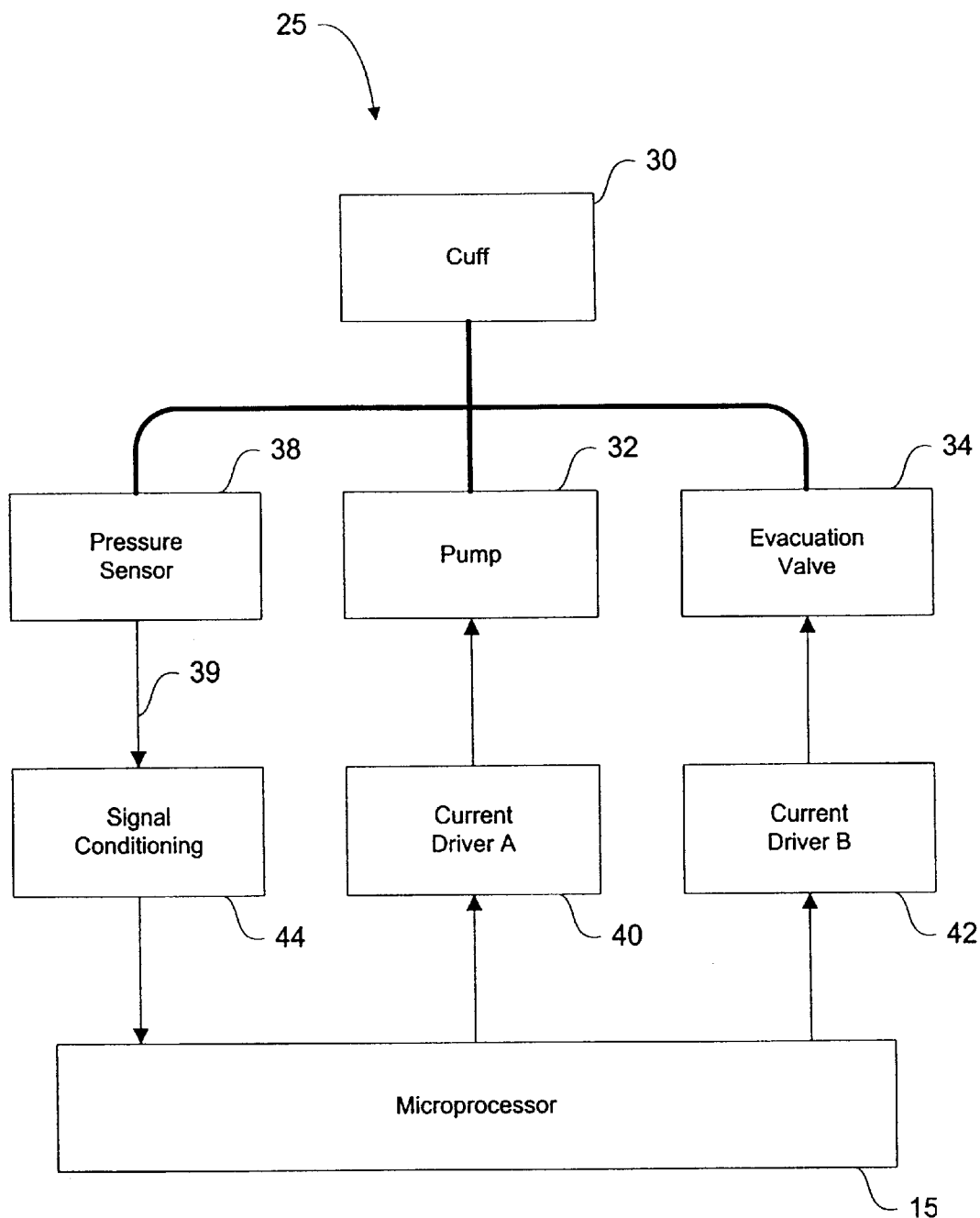
Figure 3. A Blood Pressure Measurement System

METHOD AND APPARATUS FOR MEASURING BLOOD PRESSURE BY THE OSCILLOMETRIC TECHNIQUE

TECHNICAL FIELD

The present invention relates to non-invasive methods for determining the blood pressure of a subject. More particularly, the invention relates to an improved method and apparatus for making oscillometric measurements of systolic blood pressure.

BACKGROUND

Physicians and others monitor various physiological parameters in their patients and in other subjects. Such monitoring is an important tool in evaluating patients' health. The monitoring of cardiovascular function is particularly valuable and is performed on a very widespread basis. Accurate measurement of blood pressure ("BP") and other physiological parameters allows for more precise diagnosis of medical problems. For example, accurate measurement of BP is important in the correct diagnosis of hypertension.

There are various ways to measure BP. For example, BP may be measured directly in the aorta or in other arterial blood vessels. This may be done, for example, by inserting into an arterial blood vessel a probe, such as a needle or catheter which bears, or is attached to, a pressure transducer. The transducer measures the actual pressure of the blood within the blood vessel. Although it is ideal to have directly-measured BP values for diagnostic purposes, procedures for directly measuring BP are invasive and are normally restricted to critical care environments such as operating rooms.

A variety of indirect or non-invasive techniques for measuring BP have been developed and include tonometric, auscultatory, and oscillometric methods. The tonometric method typically involves a transducer which includes an array of pressure sensitive elements positioned over a superficial artery. "Hold down" forces are applied to the transducer so as to flatten the wall of the underlying artery without occluding the artery. The pressure measured by the pressure sensitive elements is dependent upon the hold down pressure used to press the transducer against the skin of the patient.

Tonometric systems measure a reference pressure directly from a superficial artery such as the radial artery at the wrist and correlate this reference pressure with the arterial pressure. However, because the ratio of pressure outside the artery to the pressure inside the artery, known as "gain", must be known and constant, tonometric systems are not reliably accurate. Furthermore, if a patient moves, recalibration of the tonometric system is required because the system may experience a change in gain. Because the accuracy of tonometric systems depends upon the accurate positioning of a transducer over the underlying artery, placement of the transducer is critical. Furthermore, achieving proper placement of the transducer in tonometric systems is time-consuming and prone to error.

The auscultatory method involves inflating a cuff placed around a limb of the patient. Following inflation of the cuff, the cuff is permitted to deflate. Systolic blood pressure ("SBP") is taken to be the cuff pressure at which Korotkoff sounds begin to occur as the cuff is deflated. Diastolic blood pressure ("DBP") is taken to be the cuff pressure at which the Korotkoff sounds become muffled or disappear. The auscultatory method requires a judgment to be made as to when the Korotkoff sounds start and when they stop. This judgment is made when the Korotkoff sounds are at their very lowest. As a result, the auscultatory method is subject to inaccuracies due to low signal-to-noise ratio. Another recognized major disadvantage of the auscultatory method is that its accuracy degrades severely with hypotension and obesity. It is also unreliable in infants and children.

The oscillometric method also involves the inflation of a cuff placed around a limb of the patient. In this method, the cuff is deflated slowly and the pressure within the cuff is continuously monitored. The oscillometric method measures and records the amplitude of pressure oscillations in the cuff caused by blood pressure pulses in underlying arteries. As the cuff is deflated, the pressure within the cuff exhibits a certain pressure versus time waveform (FIG. 1A). The waveform can be separated into two components, a decaying component (the applied cuff pressure, C—FIG. 1C) and an oscillating component (the pressure pulse amplitudes, A—FIG. 1B).

The oscillating component may be represented by a curve known by those in the art as the "oscillometric envelope" as shown in dotted line in FIG. 1B. The oscillometric envelope starts at a low value when the cuff is inflated to a level beyond the patient's SBP and then increases to a peak value ($A_{max}$) as the cuff pressure is reduced. Once the envelope has reached $A_{max}$, the envelope then decays as the cuff pressure continues to decrease. At $A_{max}$ the mean pressure in the cuff is roughly equal to the patient's mean arterial blood pressure ("MAP").

SBP, MAP and DBP values can be determined from the data obtained by monitoring the pressure within the cuff while the cuff is slowly deflated. Again, the mean arterial blood pressure value, MAP, can be estimated as the applied cuff pressure at the point in time when the peak, $A_{max}$, of the oscillometric envelope occurs (FIG. 1C). SBP may be determined as the cuff pressure corresponding to the amplitude on the systolic side (before peak amplitude $A_{max}$) of the oscillometric envelope which is equal to a certain percentage of the peak amplitude $A_{max}$. This percentage is known by those skilled in the art as the systolic Parameter Identification Point ("PIP"), and is generally considered to be about 55%. Similarly, DBP may be determined as the cuff pressure corresponding to the amplitude on the diastolic side (after peak amplitude $A_{max}$) of the oscillometric envelope which is equal to a certain percentage of the peak amplitude $A_{max}$. This percentage is known as the diastolic PIP, which is generally considered to be close to 72%.

So, the oscillometric method uses fixed PIP's to calculate SBP and DBP values from $A_{max}$. Automated BP monitors using the oscillometric technique use these fixed PIP's in their algorithms to calculate these BP figures. It has been known for some time, however, that the oscillometric method has the disadvantage, using these fixed PIP's, of inaccuracy under the most important of circumstances, i.e., when measuring blood pressure of hypertensive patients. Specifically, using fixed PIP's, and especially a fixed systolic PIP, tends to cause most BP measuring devices to underestimate BP at higher pressures.

Baker et al. address the problem of using fixed PIP ratios in U.S. Pat. No. 5,339,819, "Method for Determining Blood Pressure Utilizing a Neural Network", and also in WO 92/03966, "Method and apparatus for determining blood pressure". Their solution to the problem is to train a neural network to recognize or map the relationship between sets of oscillometric envelope input data and the desired directly-measured blood pressure. The neural network is trained to analyse many data points on a single oscillometric envelope and thus has the advantage of not being entirely dependent upon a small number of parameters such as MAP and PIPs. However, neural networks have a disadvantage of being complex to design and train, and also costly to implement. A further disadvantage is that neural network performance is generally limited by the amount of training and the type of training data; neural networks may not perform well with new input data which they have not seen before.

Accordingly, an improved, more accurate method of blood pressure measurement which has the advantages of the oscillometric technique, but which does not underestimate higher pressures, is desirable.

SUMMARY OF INVENTION

The present invention provides an improved method and apparatus for measuring blood pressure in a subject, and in particular, systolic blood pressure.

A method according to a basic embodiment of the invention comprises the steps of: obtaining an estimate of mean arterial pressure ("MAP") by measuring the cuff pressure at the peak of the oscillometric envelope using an oscillometric technique, and optionally also obtaining an estimate of systolic blood pressure ("SBP") using a standard fixed-PIP oscillometric technique; determining, in a departure from the standard oscillometric technique, a new systolic parameter identification point ("$PIP_{SBP}$") and/or a new diastolic parameter identification point ("$PIP_{DBP}$"), these new PIP's being not fixed constants, but rather, varying functions of estimated MAP and/or estimated SBP; and then determining SBP and DBP by using an oscillometric technique, but using these new variable $PIP_{SBP}$ and $PIP_{DBP}$ in place of the usual fixed PIP's.

In a more detailed embodiment of the method, blood pressure is measured by placing a blood pressure cuff around the limb of a subject, inflating it to occlude the flow of blood in that limb, and then slowly deflating the cuff while continuously collecting instantaneous cuff pressure data; extracting from the cuff pressure data the Pulse Amplitudes which are the oscillating component of the cuff pressure and are due to the blood pressure pulses, and the average Cuff Pressure, which is the decaying component of the cuff pressure, and is due to the pressure applied to said blood pressure cuff, and representing this Cuff Pressure and Pulse Amplitude data in a pressure versus time waveform, with the sequence of discrete Pulse Amplitudes being represented by an oscillometric envelope which may be interpolated or smoothed or both for high resolution or noise reduction or both.

A value for the peak amplitude $A_{max}$ of the oscillometric envelope is determined, and the cuff pressure which corresponds in time with $A_{max}$ is also determined, this pressure representing the estimated mean arterial pressure MAP of the subject.

$PIP_{SBP}$ and $PIP_{DBP}$ values are then calculated as functions of the MAP value; the calculation $A_{SBP}=A_{max}*PIP_{SBP}$ is performed to determine a systolic amplitude value $A_{SBP}$; SBP is determined to be the cuff pressure C which corresponds in time to $A_{SBP}$ on the systolic side of the oscillometric envelope; the calculation $A_{DBP}=A_{max}*PIP_{DBP}$ is performed to determine a diastolic amplitude value $A_{DBP}$; and DBP is determined to be the cuff pressure C which corresponds in time to $A_{DBP}$ on the diastolic side of the oscillometric envelope.

In a preferred embodiment, $PIP_{SBP}$ is calculated in accordance with the following piecewise linear function:

if (MAP≦A mmHg), then $PIP_{SBP}=\alpha$;
else if (MAP≧B mmHg), then $PIP_{SBP}=\beta$;

$$\text{else } PIP_{SBP} = \alpha - \left(\frac{\alpha - \beta}{B - A} \times (MAP - A)\right)$$

where A is a pressure in the range of 90 to 110 mmHg and is preferably 100 mmHg;

α is a number in the range of 0.5 to 0.66 and is preferably 0.58;

B is a pressure in the range of 130 to 150 mmHg and is preferably 140 mmHg; and

β is a number in the range of 0.30 to 0.46 and is preferably 0.38.

In another embodiment, $PIP_{SBP}$ is calculated in accordance with the following exponential function:

$$PIP_{SBP} = A - \frac{B}{1 + Ce^{(D \times MAP)}}$$

A, B, C, and D being numeric constants where:

A is in the range of 0.50 to 0.66, and is preferably 0.58;
B is in the range of 0.04 to 0.36, and is preferably 0.2;
C is in the range of 400 to $4.3 \times 10^{15}$, and is preferably 540,000; and
D is in the range of −0.30 to −0.05, and is preferably −0.11.

In this embodiment, C and D may be related by the equation $$C = \left(\frac{1}{e^{(D \times E)}}\right)$$

where E is a constant in the range of 110 to 130.

In a third embodiment, $PIP_{SBP}$ is calculated in accordance with the following polynomial function:

$$PIP_{SBP}=A \times MAP^3+B \times MAP^2+C \times MAP+D$$

A, B, C, and D being numeric constants, where:

A is in the range of $5.90 \times 10^{-7}$ to $6.10 \times 10^{-7}$;
B is in the range of $-2.2 \times 10^{-4}$ to $-2.02 \times 10^{-4}$;
C is in the range of $1.84 \times 10^{-2}$ to $2.35 \times 10^{-2}$; and
D is in the range of $-9.00 \times 10^{-2}$ to $3.5 \times 10^{-3}$.

In this embodiment, A is most preferably $6.00 \times 10^{-7}$; B is most preferably $-2.09 \times 10^{-4}$; C is most preferably $2.06 \times 10^{-2}$; and D is most preferably $-3.22 \times 10^{-2}$.

The invention also provides an apparatus for implementing the new method, the apparatus having a microprocessor, a program memory accessible by the microprocessor, a first software program component stored within the program memory for operating the apparatus, and a data memory connected to the microprocessor for storing data from the microprocessor. A blood pressure measurement subsystem is also provided which acts under the control of the first software program component. This subsystem periodically acquires, and provides to the microprocessor, instantaneous pressure values representing the pressure within a blood pressure cuff placed on a limb of a subject.

A second software program component stored within the program memory extracts, from the instantaneous pressure values, data relating to cuff pressure and a pulse amplitude with respect to time. This data is stored by the microprocessor into the data memory. A third software program component is also provided for determining MAP from the cuff pressure and pulse amplitude data. A fourth software program component is provided for determining $PIP_{SBP}$ and $PIP_{DPB}$ as functions of the MAP. A fifth software program component is provided for determining SBP and DBP values from the pressure and amplitude data stored in the data memory, using said $PIP_{SBP}$ and $PIP_{DBP}$.

In a preferred embodiment of the system, the program memory is a ROM and the data memory may be any suitable storage means such as a RAM, EEPROM, or a disc drive. The first, second, third, fourth, and fifth software program components may conveniently be contained within a single software program.

BRIEF DESCRIPTION OF DRAWINGS

In drawings which illustrate specific embodiments of the invention, but which should not be construed as restricting the spirit or scope of the invention in any way:

FIG. 2 is a block diagram of a research apparatus incorporating a blood pressure measuring system made in accordance with one embodiment of the invention.

FIG. 3 is a block diagram of the blood pressure measurement subsystem of the system shown in FIG. 2.

DESCRIPTION

Figure 1A:
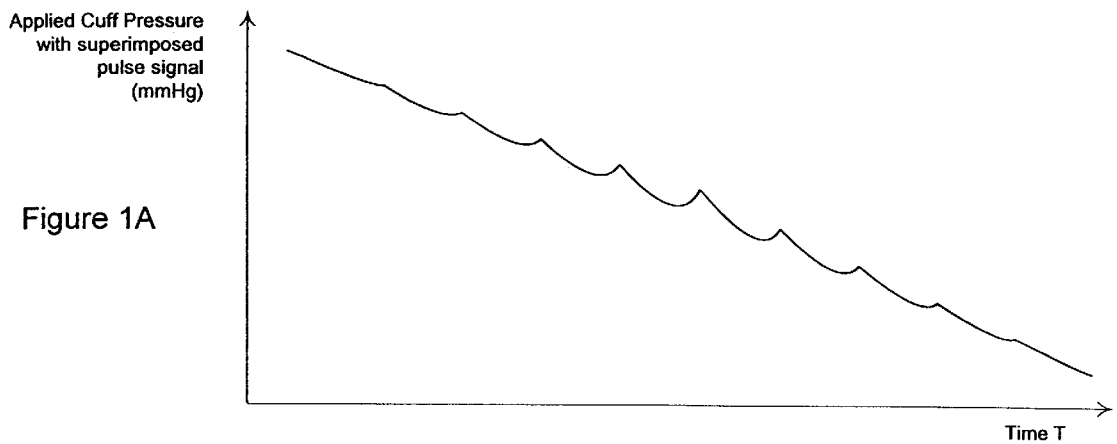
FIG. 1A is an example of a pressure versus time waveform measured within a blood pressure cuff when measuring blood pressure using the oscillometric technique.
Figure 1B:
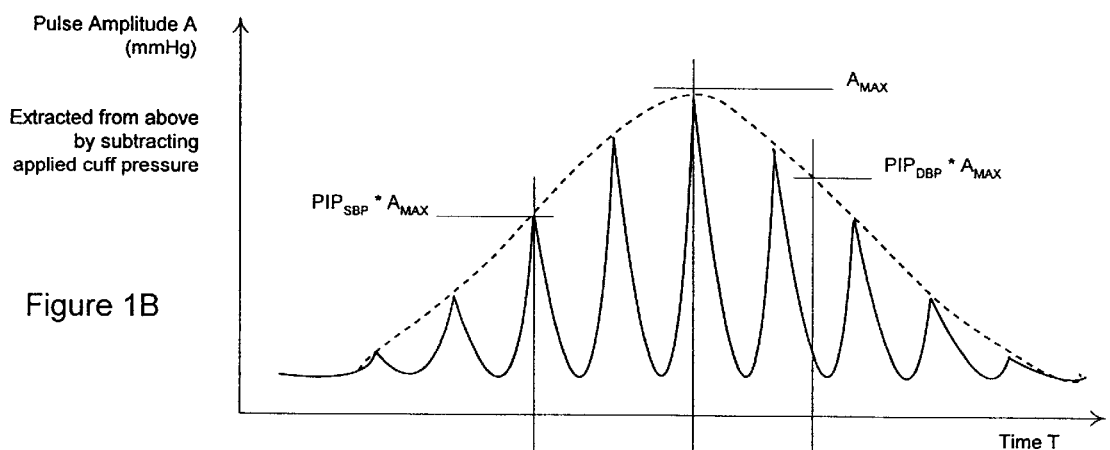
FIG. 1B is a plot of the oscillating component of the waveform shown in FIG. 1, showing the oscillometric envelope.
Figure 1C:
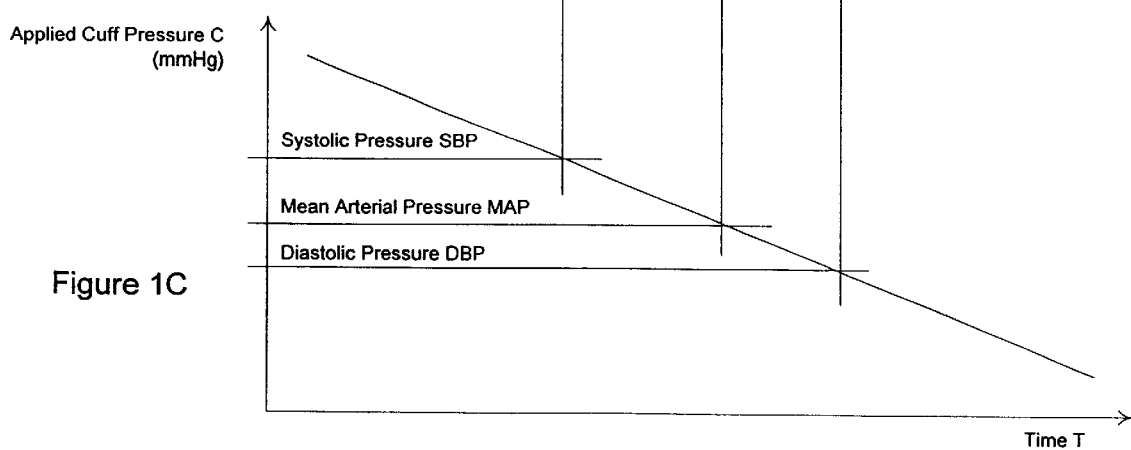
FIG. 1C is a plot of the applied cuff pressure versus time waveform measured within a blood pressure cuff when measuring blood pressure using the oscillometric technique.

As described above, many different apparatus use the oscillometric technique to determine blood pressure values. One such apparatus has been developed and manufactured by VSM MedTech Ltd. of Vancouver, Canada, and is described in co-pending U.S. patent application Ser. No. 09/328,432, filed Jun. 9, 1999, which is incorporated herein by reference.

The oscillometric method was incorporated into a research apparatus shown in some schematic detail in FIG. 2. As shown in FIG. 2, apparatus 10 comprises a microprocessor 15 which has access to a program memory 16 within which is stored a software program 18 which regulates the operation of apparatus 10. Program memory 16 preferably comprises a non-volatile memory such as a ROM, EEPROM, flash memory or the like.

Microprocessor 15 is also connected to a data memory 22 wherein microprocessor 15 can store data, including intermediate results, during execution of software program 18. Data memory 22 may comprise any suitable data storage medium including a RAM, a disc drive, or any other practical device for storing data. Program memory 16 and data memory 22 may be different areas or portions within a single physical device.

A blood pressure measurement subsystem 25, as described in detail below with reference to FIG. 3, acts under the control of software 18 which runs on microprocessor 15. Blood pressure measurement subsystem 25 comprises a cuff 30 (FIG. 3) and a means for measuring pressure within cuff 30. Subsystem 25 acquires a value for instantaneous cuff pressure once per sample period. Subsystem 25 provides the instantaneous cuff pressure values to microprocessor 15. A component 18A of software 18 extracts from the instantaneous cuff pressure data relating cuff pressure C and a pulse amplitude A, with respect to time T (collectively hereinafter referred to as TAC data). One method which may be used to extract the TAC data under software control is described in U.S. Pat. No. 5,355,890, which is incorporated herein by reference.

It will be clear that any suitable method may be used for obtaining such TAC data. Several such methods are known. For example, other embodiments of the apparatus may use hardware filtering to extract the TAC data. Techniques for extracting such data are well known to those skilled in the art. The particular technique used to obtain TAC data is largely irrelevant to the invention, and will therefore not be discussed further herein. The TAC data are stored by microprocessor 15 into data memory 22 under the control of software 18A.

In one embodiment of the invention, software 18A dynamically smooths the pulse amplitudes A, smooths the cuff pressure C, and performs artifact-reduction on the pulse amplitudes A. One method which may be used to reject artifacts is described in U.S. Pat. No. 5,505,206, which is incorporated herein by reference. Other suitable techniques for reducing artifacts are well known to those skilled in the art and may be used in this invention.

The TAC data are also transmitted by microprocessor 15 to personal computer ("PC") 50, preferably serially via UART 19, as described in detail below with reference to ascertaining PIP versus MAP relationships. This functionality is useful primarily for ascertaining PIP vs MAP relationships. Apparatus 10 also has a user interface 17, which permits a user to cause apparatus 10 to initiate and conduct BP measurements, and displays the results of measurements made by apparatus 10. It is foreseen that a commercial embodiment of the present invention may not require a separate computer 50.

FIG. 3 shows a functional block diagram of blood pressure measurement subsystem 25 and its interface with microprocessor 15 according to a presently preferred embodiment of the invention. Blood pressure measurement subsystem 25 comprises a blood-pressure cuff 30 which may be inflated to occlude the arteries in a limb of a patient; and a source of a pressurized gas or fluid, such as an electrically-operated pump 32, which is pneumatically connected to cuff 30 and can inflate cuff 30 under the control of microprocessor 15. An electrically controlled evacuation valve 34 is pneumatically connected to cuff 30. Cuff 30 can be controllably deflated by opening evacuation valve 34 under the control of microprocessor 15. A pressure sensor 38 is also pneumatically connected to cuff 30. Pressure sensor 38 provides a signal 39 representing a pressure within cuff 30 to microprocessor 15.

Blood pressure measurement subsystem 25 includes suitable interfaces between microprocessor 15 and pump 32, evacuation valve 34 and pressure sensor 38. In the illustrated embodiment, a current driver 40 allows microprocessor 15 to turn pump 32 on or off under the control of software 18. A current driver 42 allows microprocessor 15 to open or close evacuation valve 34 under control of software 18. A signal conditioner/pre-amplifier 44 amplifies and removes noise from signal 39 produced by pressure sensor 38 and converts signal 39 to digital form so that microprocessor 15 can read instantaneous pressure within cuff 30.

Software 18, which is stored in program memory 16, includes instructions which, when executed by microprocessor 15 causes microprocessor 15 to coordinate the operation of pump 32, evacuation valve 34, and take measurements of signal 39. For each measurement, software 18 causes cuff 30 to be inflated to a starting pressure and then gradually deflated.

Software component 18B determines MAP, SBP, and DBP from the TAC data acquired during cuff deflation and stored in data memory 22, using PIP information implemented in software 18B.

Figure 6:
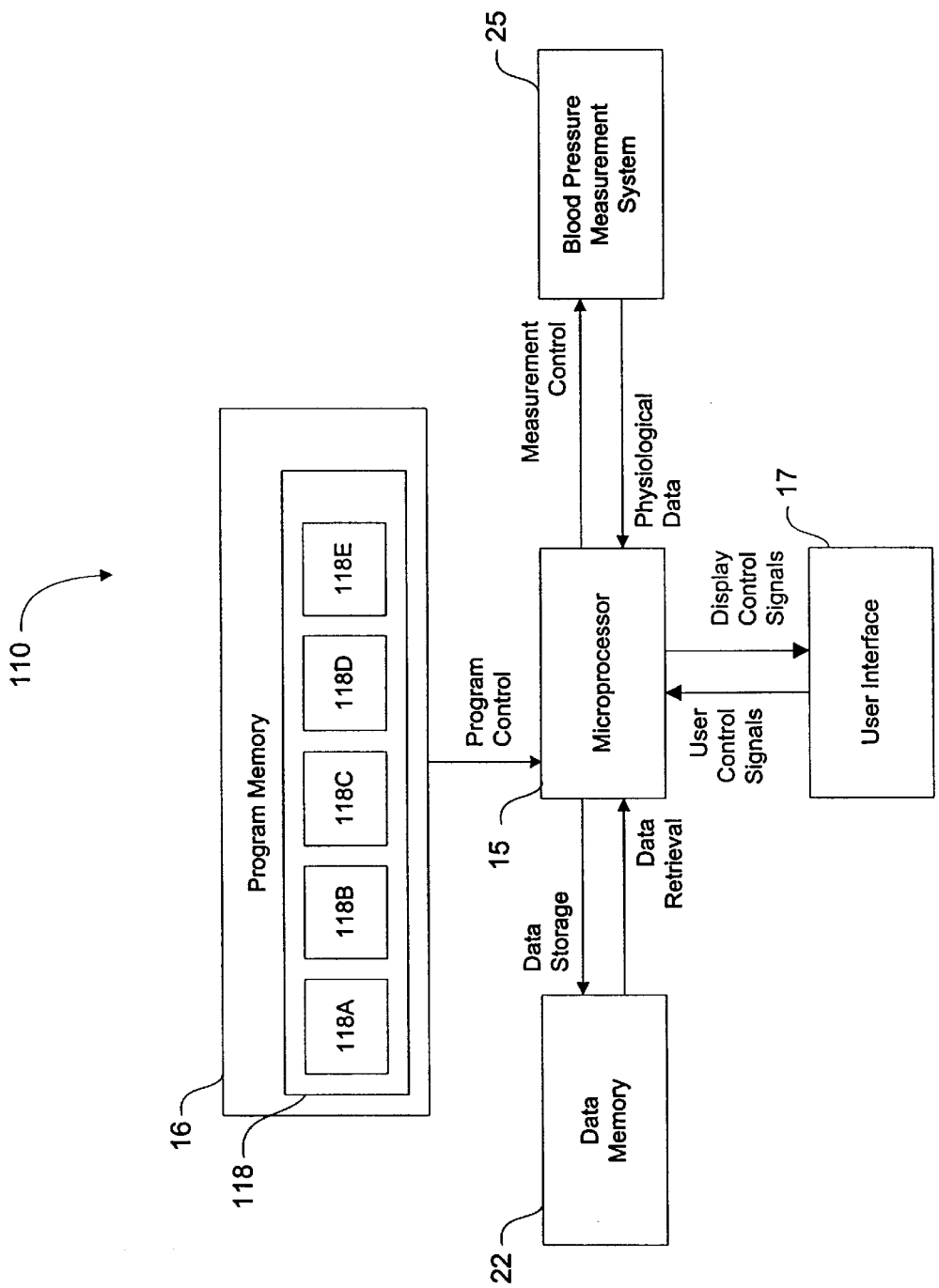
FIG. 6 is a block diagram of a blood pressure measuring apparatus made in accordance with a preferred embodiment of the invention.

In a preferred embodiment of the invention (FIG. 6), apparatus 110 includes microprocessor 15, program memory 16, software program 118, data memory 22, blood pressure measurement system 25, and user interface 17. Although this is similar to apparatus 10, additional PC 50 is not necessary for apparatus 110. Software 118 of apparatus 110 has components 118A–118E.

In this embodiment, a first software program component 118A stored within the program memory 16 acquires from blood pressure measurement subsystem 25, once per sample period, the instantaneous cuff pressure. A second software program component 118B of software 118 extracts from a plurality of instantaneous cuff pressure, data relating to time T, cuff pressure C and a pulse amplitude A (TAC data). The TAC data is stored by microprocessor 15 into data memory 22.

A third software program component 118C stored in the program memory 16 determines an estimate of MAP from the TAC data.

A fourth software component 118D stored in the program memory 16 determines the $PIP_{SBP}$ and $PIP_{DBP}$ as functions of the determined MAP, according to the new method previously described.

A fifth software component 118E stored in the program memory 16 determines SBP and DBP using the PIP's and the TAC data.

Operation

The new invention provides a method for measuring blood pressure which comprises the steps of placing a blood pressure cuff around the limb of a subject, inflating it to occlude the flow of blood in that limb, and then slowly deflating the cuff while continuously collecting instantaneous cuff pressure data; extracting from the cuff pressure data the Pulse Amplitudes which are the oscillating component of the cuff pressure and are due to the blood pressure pulses, and the average Cuff Pressure, which is the decaying component of the cuff pressure, and is due to the pressure applied to said blood pressure cuff; representing this Cuff Pressure and Pulse Amplitude data in a pressure versus time waveform, with the sequence of discrete Pulse Amplitudes being represented by an oscillometric envelope; determining a value for the largest amplitude $A_{max}$ of the oscillometric envelope, and determining also the cuff pressure which corresponds in time with $A_{max}$, this pressure representing the mean arterial pressure MAP of the subject.

The method further comprises the steps of determining $PIP_{SBP}$ and $PIP_{DBP}$ values as functions of the MAP value; performing the calculation $A_{SBP}=A_{max}*PIP_{SBP}$ to determine a systolic amplitude value $A_{SBP}$; determining SBP as the cuff pressure C which corresponds in time to $A_{SBP}$ on the systolic side of the oscillometric envelope; performing the calculation $A_{DBP}=A_{max}*PIP_{DBP}$ to determine a diastolic amplitude value $A_{DBP}$; determining DBP as the cuff pressure C which corresponds in time to $A_{DBP}$ on the diastolic side of the oscillometric envelope.

In the presently preferred embodiment $PIP_{SBP}$ is not a fixed constant, but is calculated as a function of estimated MAP, and $PIP_{DBP}$ is a fixed constant. However, in other embodiments of the invention, both $PIP_{SBP}$ and $PIP_{DBP}$ have been calculated as functions of estimated MAP and/or an estimated SBP using a standard fixed-PIP such as 0.55. The function $PIP_{SBP}(MAP)$ representing best-fit $PIP_{SBP(opt)}$ vs MAP can take a number of different mathematical forms. In a preferred embodiment the relationship between $PIP_{SBP}$ and MAP is represented by a piece-wise linear function, with MAP divided into 3 ranges. Other embodiments include the use of exponential, polynomial and other non-linear functions representing a relationship similar to the piece-wise linear functions. The important general determination is that varying PIP's may be used to calculate SBP from MAP, rather than a fixed PIP. This provides a more accurate estimate of SBP, especially at higher pressures.

Figure 7:
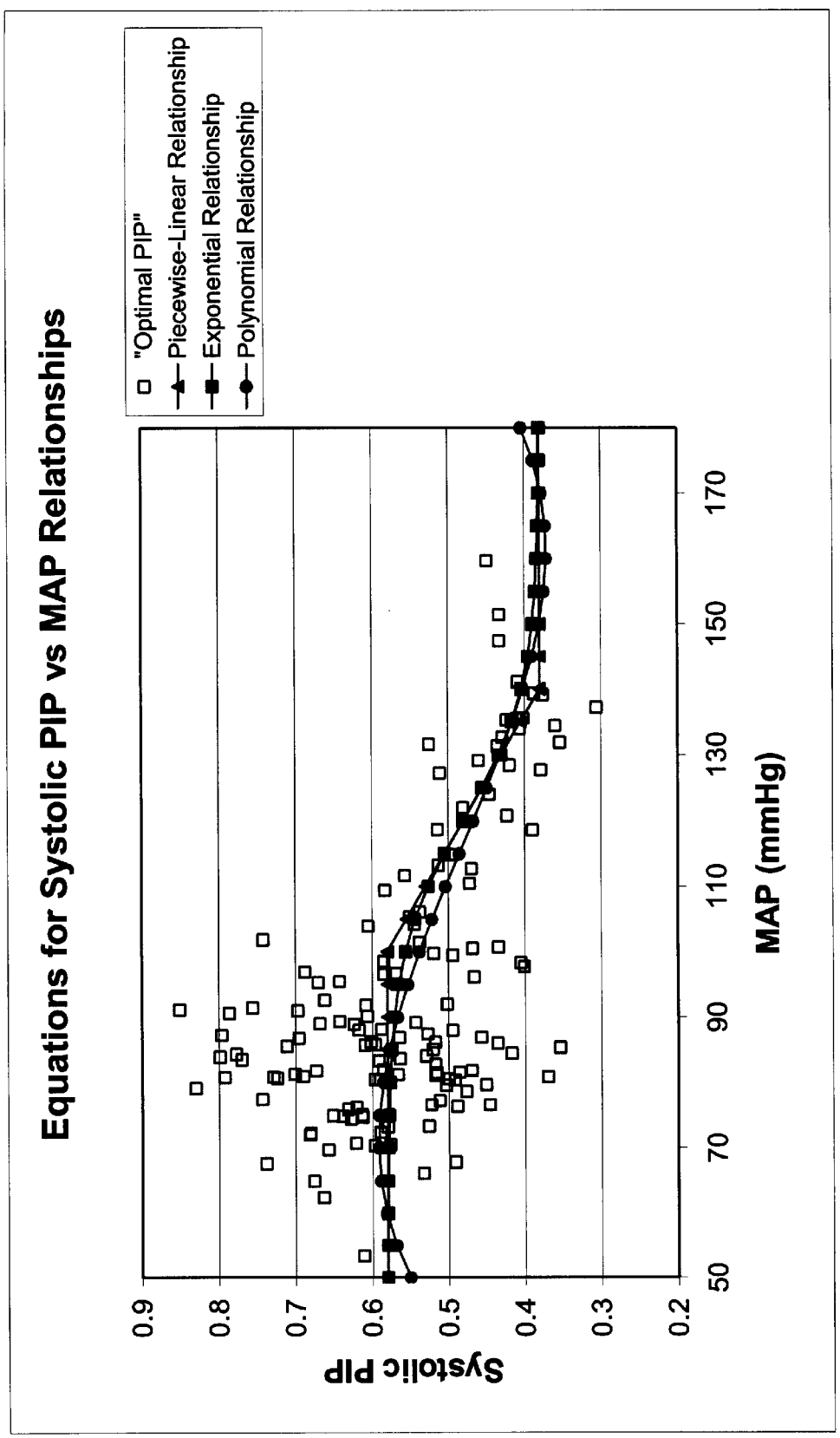
FIG. 7 is a plot of the $PIP_{SBP}$ vs. MAP relationships determined by the three example functions described herein.

FIG. 7 shows plots of the Systolic PIP vs. MAP relationships determined by the three functions described herein, as a function of MAP.

In a preferred embodiment of the new method, $PIP_{SBP}$ is calculated in accordance with the following piecewise linear function:

if (MAP≦A mmHg), then $PIP_{SBP}=\alpha$;

else if (MAP≧B mmHg), then $PIP_{SBP}=\beta$;

$$\text{else } PIP_{SBP} = \alpha - \left(\frac{\alpha-\beta}{B-A} \times (MAP-A)\right)$$

where A is a pressure in the range of 90 to 110 mmHg and is preferably 100 mmHg;

α is a number in the range of 0.5 to 0.66 and is preferably 0.58;

B is a pressure in the range of 130 to 150 mmHg and is preferably 140 mmHg; and

β is a number in the range of 0.30 to 0.46 and is preferably 0.38.

Of course, since A, B, α and β are constants, this formula can also be represented as follows:

if (MAP≦A), then $PIP_{SBP}=\alpha$, A and α being constants;

else if (MAP≧B), then $PIP_{SBP}=\beta$; B and β being constants;

else $PIP_{SBP}=\alpha-(\gamma*(MAP-A))$,

γ being a constant equal to $$\left(\frac{\alpha-\beta}{B-A}\right).$$

In another embodiment of the new method, $PIP_{SBP}$ is calculated in accordance with the following exponential function:

$$PIP_{SBP} = A - \frac{B}{1 + Ce^{(D \times MAP)}}$$

A, B, C, and D being numeric constants where:
  A is in the range of 0.50 to 0.66, and is preferably 0.58;
  B is in the range of 0.04 to 0.36, and is preferably 0.2;
  C is in the range of 400 to $4.3 \times 10^{15}$, and is preferably 540,000; and
  D is in the range of $-0.30$ to $-0.05$, and is preferably $-0.11$.

In this instance, C and D are related by the equation $$C = \left(\frac{1}{e^{(D \times E)}}\right)$$

where E is a constant between 110 and 130, and is preferably 120.

In another embodiment of the new invention, $PIP_{SBP}$ is calculated in accordance with the following polynomial function:

$$PIP_{SBP} = A \times MAP^3 + B \times MAP^2 + C \times MAP + D$$

A, B, C, and D being numeric constants, where:
  A is in the range of $5.90 \times 10^{-7}$ to $6.10 \times 10^{-7}$ and is preferably $6.00 \times 10^{-7}$;
  B is in the range of $-2.2 \times 10^{-4}$ to $-2.02 \times 10^{-4}$ and is preferably $-2.09 \times 10^{-4}$;
  C is in the range of $1.84 \times 10^{-2}$ to $2.35 \times 10^{-2}$ and is preferably $2.06 \times 10^{-2}$; and
  D is in the range of $-9.00 \times 10^{-2}$ to $3.5 \times 10^{-3}$ and is preferably $-3.22 \times 10^{-2}$.

It should be noted from FIG. 7 that these three functions produce similar curves. These curves can generally be described in the following manner: $PIP_{SBP}$ is relatively constant when MAP is in the range of between 50–100 mmHg, and is also relatively constant when MAP is in the range of between 140–180 mmHg. More particularly, in this particular Figure, $PIP_{SBP}$ has a value of:
  a) $0.58 \pm 0.08$ when 50 mmHg $\leq$ MAP $\leq$ 100 mmHg;
  b) $0.38 \pm 0.08$ when 140 mmHg $\leq$ MAP $\leq$ 180 mmHg; and
  c) an intermediate value when 100 mmHg $\leq$ MAP $\leq$ 140 mmHg.

EXAMPLE

To demonstrate the efficacy of the invention, blood pressure values determined by a research apparatus 10 using a method of fixed PIP's were compared to those determined by the invention using the new method.

Research apparatus 10 was tested in an independent validation study according to the AAMI (Association for the Advancement of Medical Instrumentation) standards, using fixed PIP values $PIP_{SBP}=0.55$ and $PIP_{DBP}=0.72$. The device performed well when judged according to the accepted standards, but, as do other devices using the oscillometric method, this device tended to underestimate the higher systolic blood pressures as depicted in the Bland-Altman plot of FIG. 4.

The Original Validation Study

In the original device validation study, 391 blood pressure measurements made by the research apparatus 10 and displayed by user interface 17 were compared with measurements made by a standard auscultatory mercury sphygmomanometer in accordance with guidelines provided by the Association for the Advancement of Medical Instrumentation(AAMI) SP10:1992, the standard-setting body for both these devices. The software 18B in the research apparatus 10 implemented the typical oscillometric technique and used the fixed systolic and diastolic PIP's of $PIP_{SBP}=0.55$ and $PIP_{DBP}=0.72$ to calculate systolic and diastolic blood pressures.

As shown in Table 1 below, comparison of the research apparatus 10 measurements with the reference standard gave a mean difference of $-0.62 \pm 6.96$ mmHg for systolic BP and $-1.48 \pm 4.80$ mmHg for diastolic BP, which is well within the AAMI standard requirements.

TABLE 1

Performance of research apparatus 10 compared to the AAMI Standard requirements

| | | SYSTOLIC | | DIASTOLIC | |
|---|---|---|---|---|---|
| | N | mean difference (mmHg) | standard deviation (mmHg) | mean difference (mmHg) | standard deviation (mmHg) |
| AAMI SP10 - 1992 requirement | | Within ±5.0 | Within 8.0 | Within ±5.0 | Within 8.0 |
| Research apparatus - Reference | 391 | −0.62 | 6.96 | −1.48 | 4.80 |

Figure 4:
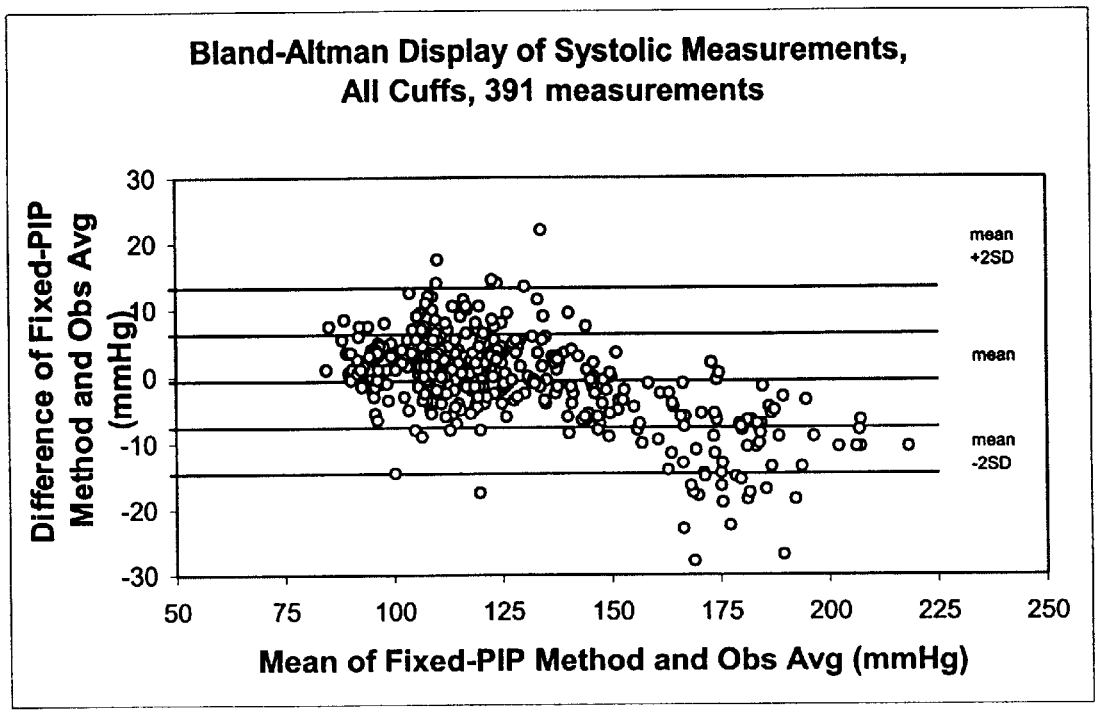
FIG. 4 is a Bland-Altman display showing the distribution of individual differences between systolic blood pressure measurements made with the standard oscillometric method (using fixed PIP's) and observer-recorded measurements for 391 sets of data.

Although the research apparatus 10 met the AAMI standard requirements, the inventors noted the tendency for the device to underestimate higher systolic blood pressures, as seen on the Bland-Altman display of individual differences (shown in FIG. 4).

As discussed earlier, it is known that the oscillometric technique, when compared with standard auscultatory methods, tends to both underestimate systolic BP and to yield high standard deviations for higher systolic pressures.

Developing the New Method

The inventors have determined that deficiencies of prior oscillometric devices can be overcome by using variable values for PIP, based upon relationships between PIP vs estimated MAP and PIP vs estimated SBP. During the aforementioned validation study, TAC data from each of the 391 blood pressure measurements conducted during the study was saved in a computer memory. The data was then used to ascertain PIP vs MAP and PIP vs SBP relationships. Data acquisition software 52, running on PC 50 received TAC data serially from the microprocessor 15 via UART 19; the TAC data for each BP measurement performed in the study was saved as a separate disk file. The file name, corresponding observer results, and the corresponding research apparatus results were all tabulated.

To develop the new method, the TAC data and the observer results saved from the original validation study were divided into training and test data sets, the training set having 136 records, and the test set having 255 (corresponding to the minimum number of required readings in order to conform with the requirements of the AAMI standard—3 paired readings for each of 85 patients representing the various population ranges).

Data analysis software 53 (a C program, in this instance) running on PC 50 was then used on the training set of data to determine MAP vs SBP and MAP vs DBP relationships. For each observer systolic BP reading (which was actually the average of the two observer auscultation readings), there was a corresponding systolic PIP with which a research apparatus 10 would provide the exact same systolic reading.

For the entire training set of data, software 53 read one file at a time, both TAC data and observer results, and solved for this "optimum" PIP. That is, software 53 determined by interpolation the time at which the applied cuff pressure C was equal to the observer-recorded SBP. Software 53 then interpolated the pulse amplitude $A_{SBP}$ at that instant in time, and then found the optimum ratio $PIP_{SBP(opt)} = A_{SBP}/A_{max}$. Similarly, software 53 determined by interpolation the time at which the applied cuff pressure C was equal to the observer-recorded DBP. Software 53 then interpolated the pulse amplitude $A_{DBP}$ at that time, and then found the ratio $PIP_{DBP(opt)} = A_{DBP}/A_{max}$. Software 53 further determined the cuff pressure C which corresponded in time to $A_{max}$, and which represented MAP. For each file, software 53 created a file record comprising: research apparatus SBP, observer-recorded SBP, $PIP_{SBP(opt)}$, research apparatus DBP, observer-recorded DBP, $PIP_{DBP(opt)}$, and MAP.

In this instance, software 53's output file was imported into a mathematical analysis program running on a personal computer, and the relationships between $PIP_{SBP(opt)}$ and MAP and/or research apparatus SBP, and $PIP_{DBP(opt)}$ and MAP and/or research apparatus DBP were analyzed. Various relationships were found and evaluated for "goodness of fit".

To evaluate these relationships, they were implemented in BP-determining software 54, running on PC 50. The training data was used again, this time to verify the ascertained relationships. The input file to software 54 comprised records consisting of: TAC data file name, observer-recorded SBP, research apparatus SBP, observer-recorded DBP, and research apparatus DBP. Software 54 running on PC 50 read the TAC data file corresponding to each input file record, calculated SBP and DBP using the newly-ascertained relationships, and appended to each record in the input file the newly-calculated SBP and DBP.

Software 54's output file was imported into a mathematical analysis program running on a personal computer, and was statistically analyzed—average error and standard deviation for the newly-calculated SBP and DBP was evaluated for each assumed relationship until a desired result was obtained—in this case an improvement in standard deviation of the difference between the automated BP reading and the reference reading provided by the auscultation method over the previous fixed-PIP scheme.

From this activity the inventors developed the following piecewise linear function:

if (MAP$\leq$A mmHg), then $PIP_{SBP} = \alpha$;
else if (MAP$\geq$B mmHg), then $PIP_{SBP} = \beta$;

$$\text{else } PIP_{SBP} = \alpha - \left(\frac{\alpha - \beta}{B - A} \times (MAP - A)\right)$$

where A is a pressure in the range of 90 to 110 mmHg and is preferably 100 mmHg;
  α is a number in the range of 0.5 to 0.66 and is preferably 0.58;
  B is a pressure in the range of 130 to 150 mmHg and is preferably 140 mmHg; and
  β is a number in the range of 0.30 to 0.46 and is preferably 0.38.

It was also determined that by using the described piecewise linear relationship between $PIP_{SBP}$ and MAP with A=100 mmHg, B=140 mmHg, α=0.58, and β=0.38, the standard deviation of the difference between the automated BP measurement and the auscultatory reference improved by 2.38 mmHg compared with the standard deviation obtained by using the fixed-PIP relationship, as shown below.

Fixed $PIP_{SBP}$(0.55) New piecewise-linear $PIP_{SBP}$ Average Difference,

| | | |
|---|---|---|
| research apparatus - ref: | 0.62 | −0.25 |
| Standard Deviation: | 6.96 | 4.58 |

Once the piecewise-linear relationship was determined, and tested on the training data, software 54, running on PC 50 was then used to further validate the new method, this time using the test data set.

Validation of the New Method

Once the new algorithm was developed on the training set, the test set of 255 measurements was used to objectively evaluate the performance of the algorithm on "new" data. The performance results of the new algorithm were analyzed according to the AAMI standard. The overall mean difference between the reference standard systolic and diastolic blood pressure and the new algorithm as implemented in apparatus 10 (reference-apparatus 10) is shown in Table 2.

TABLE 2

Performance of research apparatus 10 with the new method, compared to the AAMI Standard requirements

| | | SYSTOLIC | | DIASTOLIC | |
|---|---|---|---|---|---|
| | N | mean difference (mmHg) | standard deviation (mmHg) | mean difference (mmHg) | standard deviation (mmHg) |
| AAMI SP10 - 1992 | | Within ±5 | Within 8 | Within ±5 | Within 8 |
| New Method - Reference | 255 | −0.16 | 5.13 | −1.41 | 4.67 |

The new invention provided an improvement in standard deviation of the difference between the automated BP reading and the reference reading provided by the auscultation method over the previous fixed-PIP scheme. These results improved upon the results with the original algorithm using fixed PIP's (Table 1), and continued to meet the AAMI standard requirements.

Figure 5:
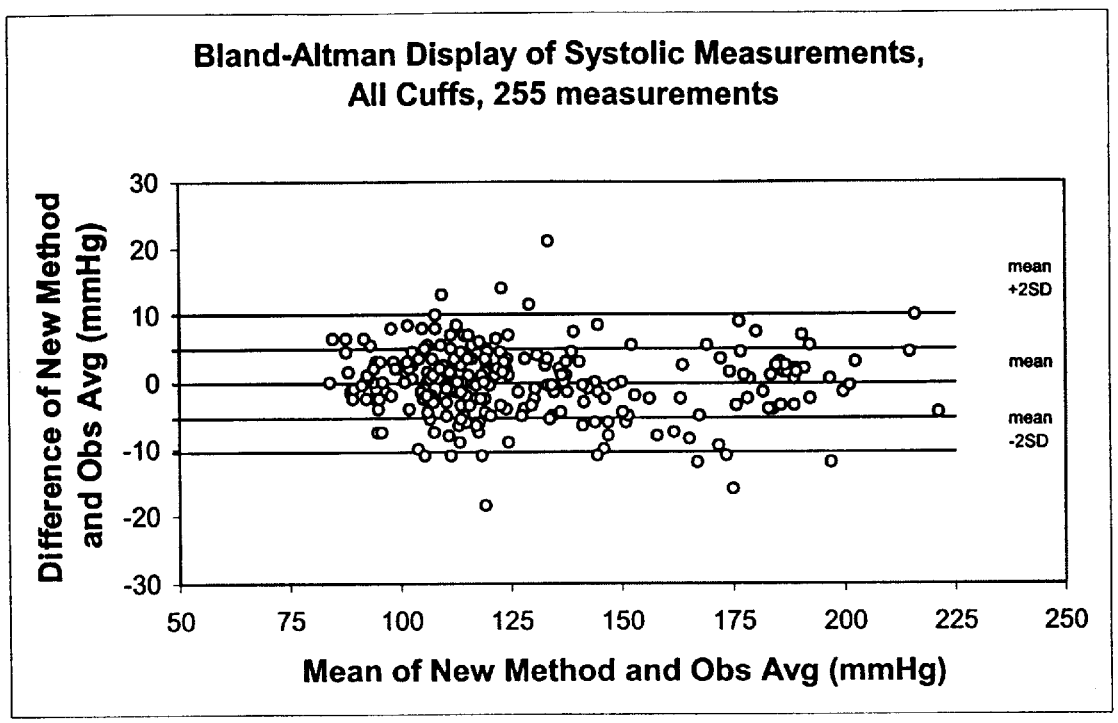
FIG. 5 is a Bland-Altman display showing the distribution of individual differences between systolic blood pressure measurements made with the new oscillometric method (using the $PIP_{SBP}$ function described herein) of the present invention and observer-recorded measurements for 255 sets of data.

In FIG. 5 the Bland-Altman display of individual measurements for systolic blood pressure (N=255) shows that the differences of the reference standard and new algorithm blood pressures are clustered around 0 over the whole range of systolic readings, unlike the results shown in FIG. 4.

The new algorithm was then implemented in microprocessor 15, and this implementation was validated by regression testing ie. performance comparison against the same algorithm implemented in software 54 running on PC 50. The expectation was that for a given BP measurement, the result determined by the algorithm implemented in microprocessor 15 would be equal (within rounding error) to the results determined by software 54 running on PC 50.

The regression test was performed with the assistance of a patient simulator (a Biotek™ BP Pump), to which apparatus 10 was connected. 85 BP measurements were performed, with simulator settings being varied for each measurement, such that the AAMI Standard requirement for "population" was met. As in the original validation study, data acquisition software 52 running on PC 50 received TAC data serially from the microprocessor 15 with the new algorithm of the present invention implemented; the TAC data for each BP measurement performed was saved as a separate disk file. The file name and the corresponding research apparatus BP results were tabulated for the input file for software 54. Then, software 54 running on PC 50 read the TAC data file corresponding to each input file record, calculated SBP, and appended to each record in the input file the calculated SBP.

Examination of software 54's output file showed no differences whatsoever between the BP results as determined by the software 54 and the microprocessor 15 implementations of the algorithm, thereby proving by regression that both implementations of the new algorithm are equivalent. The results shown in Table 2, therefore, also apply to the apparatus 110 for commercialization, as apparatus 110 also includes the new algorithm implemented in microprocessor 15.

As will be apparent to those skilled in the art in light of the foregoing disclosure, many alterations and modifications are possible in the practice of this invention without departing from the spirit or scope thereof. For example, it will be recognized that the means by which $A_{max}$ and MAP are determined, prior to the determination of SBP and/or DBP by calculating a PIP by the given function, is not important to the invention. There may be a variety of ways in which these values may be determined which all fall within the scope of the present invention. Further, it should be noted that it is not completely necessary to compute values as described herein with reference only to $A_{max}$. It is foreseen that it should be possible to compute $PIP_{SBP}$ values from any reference point on the oscillometric envelope.

Further, it should be noted that the computing function need not necessarily be done by performing the aforementioned calculations for each and every blood pressure measurement; rather, the computing function can be done by look-up table.

Accordingly, the scope of the invention is to be construed in accordance with the substance defined by the following claims.

What is claimed is:

1. A method for calculating the systolic blood pressure of a subject using the oscillometric technique, the method comprising:
    a) obtaining a value for the peak amplitude $A_{max}$ of an oscillometric envelope;
    b) determining a cuff pressure, CP, which corresponds in time with $A_{max}$, this pressure representing the MAP of the subject;
    c) computing a variable value $PIP_{SBP}$ as a function of MAP;
    d) performing the calculation $A_{sbp}=A_{max}*PIP_{SBP}$ to determine a systolic amplitude value $A_{sbp}$ along the oscillometric envelope; and
    e) determining the cuff pressure C which corresponds in time to $A_{sbp}$, this value representing the systolic blood pressure (SBP) of the subject.

2. A method for measuring blood pressure, comprising:
    a) placing a blood pressure cuff around the limb of a subject, inflating it, and monitoring the pressure within said cuff as said cuff is slowly deflated;
    b) collecting Time, Cuff pressure and Pressure pulse amplitude data during this deflation time;
    c) representing said Time, Cuff pressure and Pressure pulse amplitude data in a pressure versus time waveform;
    d) from this pressure versus time waveform, deriving an oscillating component due to blood pressure pulses;
    e) representing said oscillating component by an oscillometric envelope;
    f) obtaining a value for the peak amplitude $A_{max}$ of said oscillometric envelope;
    g) determining a cuff pressure CP which corresponds in time with $A_{max}$, this pressure representing the mean arterial pressure (MAP) of the subject;
    h) calculating a $PIP_{SBP}$ value from said MAP pressure;
    i) performing the calculation $A_{sbp}=A_{max}*PIP_{SBP}$ to determine a systolic amplitude value $A_{sbp}$ along said oscillometric envelope;
    j) determining the cuff pressure C which corresponds in time to $A_{sbp}$; and
    k) displaying cuff pressure C, this value representing the systolic blood pressure (SBP) of the subject.

3. A system for measuring blood pressure by the oscillometric technique, said system comprising:
    a) a microprocessor;
    b) a program memory accessible by said microprocessor;
    c) a first software program component stored within said program memory for operating said microprocessor;
    d) a data memory connected to said microprocessor for storing data from said microprocessor;
    e) a blood pressure measurement subsystem acting under the control of said first software program component, said subsystem acquiring once per sample period, and providing to said microprocessor, an instantaneous pressure value representing the blood pressure within a blood pressure cuff placed on a subject;
    f) a second software program component stored within said program memory for extracting, from said instantaneous pressure value, data relating to time T, cuff pressure C and a pulse amplitude A, said time, pressure and amplitude data stored by said microprocessor into said data memory;
    g) a systolic blood pressure determiner comprising a third software program component for determining MAP from said time, pressure and amplitude data, for determining PIPs from said MAP, and for determining SBP and DBP values from said PIPs; and
    h) a user interface allowing a user to provide input to said system and to receive output from said system.

4. The blood pressure measuring system of claim 3, wherein said first, second and third software program components are contained within a single software program.

5. A method for determining a blood pressure of a subject, the method comprising:
    a) using an oscillometric technique to obtain oscillometric data;
    b) estimating mean arterial pressure (MAP), or estimating systolic blood pressure (SBP) from said oscillometric data;
    c) determining $PIP_{SBP}$, $PIP_{DBP}$, or both $PIP_{SBP}$ and $PIP_{DBP}$ values as functions of estimated MAP or estimated SBP; and
    d) using said $PIP_{SBP}$ and/or $PIP_{DBP}$ values in an oscillometric technique to determine SBP and/or DBP.

6. The method claimed in claim 5 wherein MAP is obtained by:
    a) obtaining an oscillometric envelope from the oscillometric data;
    b) finding a peak value $A_{max}$ of said oscillometric envelope; and
    c) obtaining an estimated mean arterial pressure (MAP) by determining a cuff pressure which corresponds in time with $A_{max}$.

7. The method claimed in claim 5 wherein the estimated SBP is obtained in a way in which systolic pressure is typically obtained in the standard oscillometric technique in which a fixed PIP is used.

8. A method for measuring blood pressure, comprising the steps of:
   a) applying a blood pressure cuff around a limb of a subject, inflating said cuff to occlude the flow of blood in that limb, and then deflating the cuff while collecting Cuff Pressure Data;
   b) extracting Pulse Amplitudes from said Cuff Pressure Data, the Pulse Amplitudes comprising the oscillating component due to the blood pressure pulse;
   c) representing the sequence of said Pulse Amplitudes by an envelope;
   d) obtaining a peak value of said envelope, $A_{max}$;
   e) determining a cuff pressure which corresponds in time with $A_{max}$, this pressure being an estimate of the mean arterial pressure (MAP) of the subject;
   f) determining the $PIP_{SBP}$, $PIP_{DBP}$, or both $PIP_{SBP}$ and $PIP_{DBP}$ values from said MAP pressure; and
   g) determining the systolic blood pressure according to said $PIP_{SBP}$, or the diastolic pressure according to said $PIP_{DBP}$.

9. The method claimed in any of claims 1, 2, 5, or 8 wherein:
   a) if (MAP$\leq$A), then $PIP_{SBP}=\alpha$, A and $\alpha$ being constants;
   b) else if (MAP$\geq$B), then $PIP_{SBP}=\beta$; B and $\beta$ being constants; and
   c) else $PIP_{SBP}=\alpha-(\gamma*(MAP-A))$,
   $\gamma$ being a constant equal to
   $$\left(\frac{\alpha-\beta}{B-A}\right).$$

10. The method of claim 9, wherein:
    a) A is between 90 and 110 mmHg;
    b) $\alpha$ is between 0.5 and 0.66;
    c) B is between 130 and 150 mmHg; and
    d) $\beta$ is between 0.30 and 0.46.

11. The method claimed in claim 10 wherein:
    a) A is 100 mmHg, and $\alpha$ is 0.58; and
    b) B is 140 mmHg, $\beta$ and 0.38.

12. The method claimed in any of claims 1, 2, 5, or 8 wherein $PIP_{SBP}$ is calculated as follows:
    $$PIP_{SBP} = A - \frac{B}{1 + Ce^{(D \times MAP)}}$$

A, B, C, and D being constants where:
    A is between 0.50 and 0.66;
    B is between 0.04 and 0.36;
    C is between 400 and $4.3 \times 10^{15}$; and
    D is between $-0.30$ and $-0.05$.

13. The method of claim 12 wherein C and D are related by the equation
    $$C = \left(\frac{1}{e^{(D \times E)}}\right)$$
    where E is a constant between 110 and 130.

14. The method of claim 12 wherein:
    a) A is 0.58;
    b) B is 0.2;
    c) C is 540,000; and
    d) D is $-0.11$.

15. The method claimed in any of claims 1, 2, 5, or 8 wherein $PIP_{SBP}$ is calculated as follows:
    $$PIP_{SBP} = A \times MAP^3 + B \times MAP^2 + C \times MAP + D$$

A, B, C, and D being constants, where:
    A is between $5.90 \times 10^{-7}$ and $6.10 \times 10^{-7}$;
    B is between $-2.2 \times 10^{-4}$ and $-2.02 \times 10^{-4}$;
    C is between $1.84 \times 10^{-2}$ and $2.35 \times 10^{-2}$; and
    D is between $-9.00 \times 10^{-2}$ and $3.5 \times 10^{-3}$.

16. The method of claim 15 wherein
    a) A is $6.00 \times 10^{-7}$;
    b) B is $-2.09 \times 10^{-4}$;
    c) C is $2.06 \times 10^{-2}$; and
    d) D is $-3.22 \times 10^{-2}$.

17. An apparatus for measuring blood pressure, said apparatus comprising:
    a) a microprocessor;
    b) a program memory accessible by said microprocessor;
    c) a first software program component stored within said program memory;
    d) a data memory connected to said microprocessor;
    e) a blood pressure measurement subsystem acting under the control of said first software program component, said subsystem periodically acquiring, and providing to said microprocessor, instantaneous pressure values representing the pressure within a blood pressure cuff placed on a subject, and storing said values from said microprocessor in said data memory;
    f) a second software program component stored within said program memory for extracting, from plurality of said instantaneous pressure values, data relating to pulse amplitudes A and their corresponding cuff pressures C, said A and C data stored by said microprocessor into said data memory;
    g) a third software program component stored within said program memory for determining the MAP from said A and C data;
    h) a fourth software program component stored within said program memory for determining the PIPs based on said MAP; and
    i) a fifth software program component stored within said program memory for determining the SBP and DBP based on said PIPs and said A and C data.

18. The apparatus of claim 17, wherein said first, second, third, fourth and fifth software program components are contained within a single software program.

19. An apparatus for measuring blood pressure, said apparatus comprising:
    a) means for collecting TAC data from a subject;
    b) means for determining MAP of said subject from said TAC data;
    c) means for determining $PIP_{SBP}$, and optionally $PIP_{DBP}$, as a function of said MAP; and
    d) means for computing SBP, and optionally DBP, from said $PIP_{SBP}$ and said $PIP_{DBP}$ values, respectively.

20. A method for measuring blood pressure, comprising the steps of:
   a) applying a blood pressure cuff around a limb of a subject, inflating said cuff to occlude the flow of blood in that limb, and then deflating the cuff while collecting Cuff Pressure Data;
   b) extracting from said Cuff Pressure Data the Pulse Amplitudes, which are the oscillating component due to the blood pressure pulse;
   c) representing the sequence of said discrete Pulse Amplitudes by an oscillometric envelope;
   d) obtaining a reference point on said envelope;
   e) computing $PIP_{SBP}$ and, optionally, $PIP_{DBP}$ values from said reference point; and
   f) determining a reference time point corresponding to $PIP_{SBP}$ and, optionally, $PIP_{DBP}$; and
   g) determining a cuff pressure value corresponding to said reference time point.

21. The method of claims 1, 2, 5 or 8 wherein $PIP_{SBP}$ is calculated as a function of MAP, the function producing a curve wherein $PIP_{SBP}$ is relatively constant when MAP is in the range of between 50–100 mmHg, and is also relatively constant when MAP is in the range of between 140–180 mmHg.

22. The method of claim 21 wherein $PIP_{SBP}$ has a value of:
   a) 0.58±0.08 when 50 mmHg≦MAP≦100 mmHg;
   b) 0.38±0.08 when 140 mmHg≦MAP≦180 mmHg; and
   c) an intermediate value when 100 mmHg≦MAP≦140 mmHg.

* * * * *